(12) United States Patent
Miyazawa et al.

(10) Patent No.: US 7,875,692 B2
(45) Date of Patent: Jan. 25, 2011

(54) POLYSILOXANE HAVING PHOSPHORYLCHOLINE GROUP AND PROCESS FOR PRODUCING THE SAME

(75) Inventors: Kazuyuki Miyazawa, Yokohama (JP); Takashi Oka, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 1223 days.

(21) Appl. No.: 10/534,399

(22) PCT Filed: Nov. 20, 2003

(86) PCT No.: PCT/JP03/14784

§ 371 (c)(1),
(2), (4) Date: May 10, 2005

(87) PCT Pub. No.: WO2004/048444

PCT Pub. Date: Jun. 10, 2004

(65) Prior Publication Data

US 2006/0020098 A1 Jan. 26, 2006

(30) Foreign Application Priority Data

Nov. 25, 2002 (JP) ............................ 2002-340319

(51) Int. Cl.
*C08G 77/04* (2006.01)
*C08G 77/26* (2006.01)
(52) U.S. Cl. ......................................... 528/28; 528/38
(58) Field of Classification Search .................. 528/28, 528/38
See application file for complete search history.

(56) References Cited

U.S. PATENT DOCUMENTS 4,203,893 A * 5/1980 Pery et al. .................... 530/401
5,369,012 A * 11/1994 Koontz et al. ............... 435/7.92
6,828,029 B1 * 12/2004 Lewis et al. .................. 428/446

FOREIGN PATENT DOCUMENTS

| JP | 62-258390 | * 11/1987 |
| JP | 2001-106749 A | 11/1997 |
| JP | 09-296019 A | 4/2001 |

OTHER PUBLICATIONS

Liberda, J. et al. Chimia 1999, 53, 528-532.*
Yamada, M.; Li, Y.; Nakaya, T. Macromolecules 1995, 28, 2590-2591.*
Stults, N. L. et al. Analytical Biochemistry 1987, 161, 567-573.*
Office Action issued in corresponding Taiwanese patent application serial No. 09521007550.

* cited by examiner

*Primary Examiner*—Randy Gulakowski
*Assistant Examiner*—Robert Loewe
(74) *Attorney, Agent, or Firm*—Townsend & Banta

(57) ABSTRACT

A polysiloxane having a phosphorylcholine group represented by the following general formula (1).

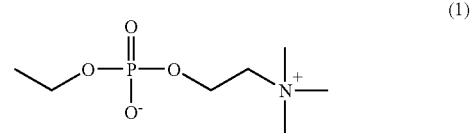

To develop a method to obtain a polysiloxane having a phosphorylcholine group with ease and great versatility and provide a polysiloxane having a phosphorylcholine group in order to obtain a polysiloxane that has a wide range of application as a biocompatible material and a cosmetic material.

3 Claims, 6 Drawing Sheets

POLYSILOXANE HAVING PHOSPHORYLCHOLINE GROUP AND PROCESS FOR PRODUCING THE SAME

TECHNICAL FIELD

The present invention relates to a polysiloxane containing a phosphorylcholine group and a method for manufacturing it. The polysiloxane of the present invention is superior in biocompatibility and moisture retention, and is useful as a polymer material for medical use. Specifically, it is utilized in artificial organs, biomembranes, coating agents for medical tools, drug delivery, cosmetic ingredients, etc.

BACKGROUND ART

Polymers containing phosphorylcholine groups have been developed as biocompatible materials. Polymers having phosphorylcholine groups have been synthesized mainly as follows: acryl type monomers mainly having hydroxyl groups and 2-chloro-1,3,2-dioxaphosphorane-2-oxide are brought into reaction and then trimethylamine is used to turn the reaction product into quaternary ammonium to synthesize monomers having a phosphorylcholine structure, which are then polymerized (refer to the following Patent Documents, for example).

Patent Document 1 describes the preparation of a copolymer of 2-methacroyloxyethylphosphorylcholine and methacrylate, and Patent Document 2 describes the preparation of a homopolymer of 2-methacryloyloxyethyl phosphorylcholine.

Patent Document 3 discloses a cosmetic in which powder coated with a homopolymer or copolymer of 2-methacryloyloxyethyl phosphorylcholine is used as a cosmetic powder to improve moisture retention and adhesion on the skin.

Patent Document 4 describes a polymer prepared by means of the graft polymerization of 2-methacryloyloxyethyl phosphorylcholine on water soluble cellulose; this polymer is utilized as a polymer having blood compatibility.

Patent Document 1: Japanese Patent Laid-Open H9-3132 bulletin
Patent Document 2: Japanese Patent Laid-Open H10-298240 bulletin
Patent Document 3: Japanese Patent Laid-Open H7-118123 bulletin
Patent Document 4: Japanese Patent Laid-Open H5-345802 bulletin A polyalkylsiloxane having phosphorylcholine groups in its main chain has not been reported.

Due to the monomer solubility issues when introducing the hydrophobic groups into the polymer, the polymer preparation method in which monomers having a phosphorylcholine group are polymerized requires the use of an organic solvent known as a chain transfer catalyst such as methanol, ethanol, and chloroform as a polymerization solvent, which makes it difficult to produce high molecular weight polymers.

Also, there is a problem in that the steric hindrance of the phosphorylcholine group reduces the polymerization yield or makes it impossible to obtain the desired polymer Also, the monomer synthesis reaction has to be conducted under strictly anhydrous conditions, which complicates the technique.

In view of the description above, the inventors conducted earnest research to obtain a polysiloxane that has a wide application range in biocompatible materials and cosmetic ingredients, and completed the present invention by discovering that a polysiloxane having a phosphorylcholine group can be obtained easily and with a high versatility by reacting a compound containing phosphorylcholine groups with a polysiloxane having a functional group that reacts with this compound, which leads to a macromolecular reaction in the main chains or side chains of the polymer.

DISCLOSURE OF INVENTION

That is, the present invention provides a polysiloxane having a phosphorylcholine group represented by the following general formula (1).

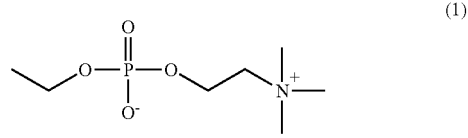

(1)

Also, the present invention provides a polysiloxane having repeating units represented by the following formulas (5), (6), and (7) obtained by introducing the phosphorylcholine group represented by said formula (1) to some or all of the amino groups of amino-modified polysiloxane having repeating units a and b or repeating units a, b, and c represented by the following formulas (2), (3), and (4).

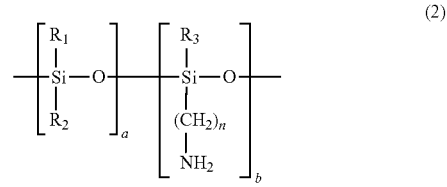

(2)

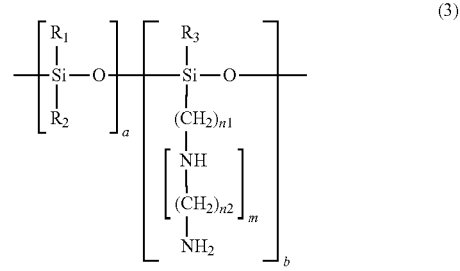

(3)

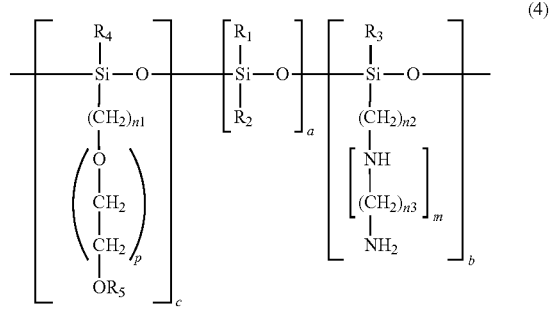

(4)

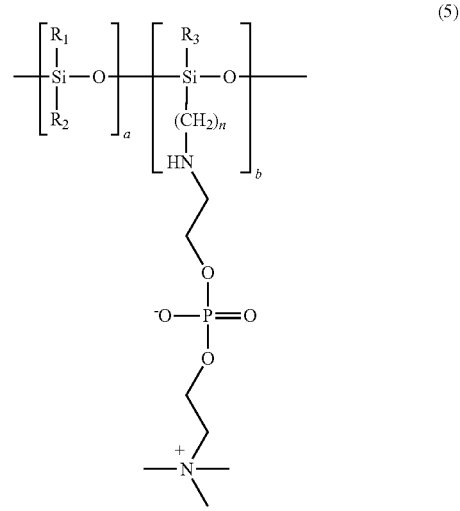

(5)

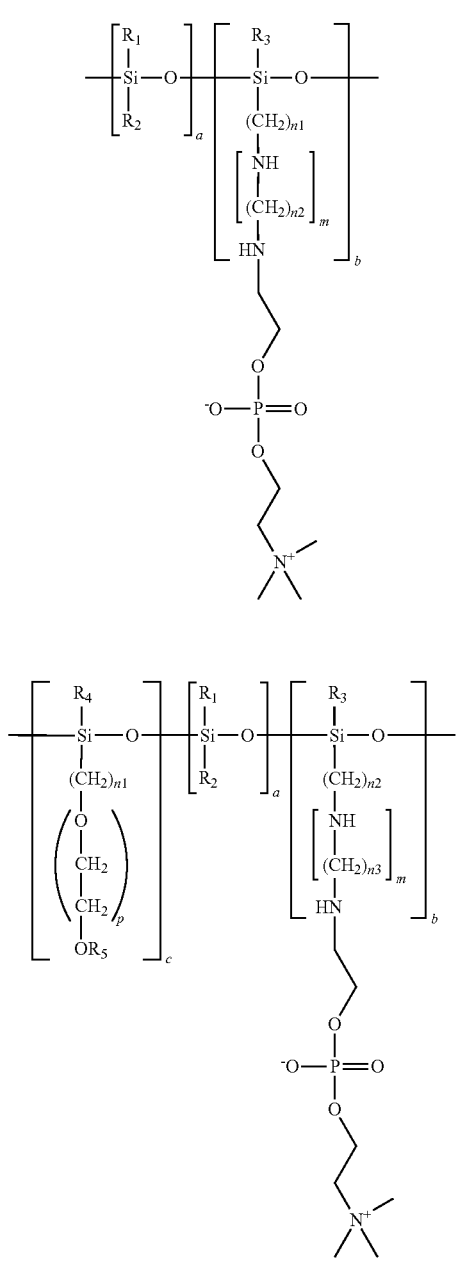

$R_1$, $R_2$, $R_3$, and $R_4$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $R_5$ denotes a hydrogen atom or an alkyl group having 1-22 carbon atoms. n denotes an integer 1-22. $n_1$, $n_2$, and $n_3$, independently of each other, denote an integer 1-22. m denotes an integer 0-10. p denotes an integer 1-30.

Furthermore, the present invention provides a method for manufacturing a polysiloxane having phosphorylcholine groups wherein the aldehyde derivative-containing compound obtained by the oxidative ring-opening reaction of glycerophosphorylcholine is added to a polysiloxane containing amino groups.

BEST MODE FOR CARRYING OUT THE INVENTION

Figure 1:
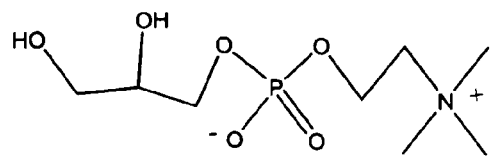
FIG. 1 shows a scheme for preparing a monofunctional aldehyde derivative having a phosphorylcholine group.
Figure 1:
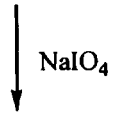
Figure 1:
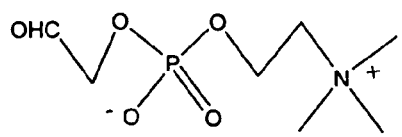

The present invention is described in detail below.

The polysiloxane having a phosphorylcholine group of the present invention is prepared with the following method.

1: Amino groups are introduced to any polysiloxane by using a prior art method or a method that will be developed in the future. Commercial amino-modified polysiloxane having primary amines or secondary amines may be used.

2: An aldehyde derivative or hydrate derivative obtained by the oxidative ring-opening reaction of glycerophosphorylcholine is added to a polysiloxane having amino groups by means of a reductive amination reaction.

This preparation method has significant advantages in that the introduction yield is high and the introduction ratio can be controlled easily.

For example, the introduction ratio of the phosphorylcholine can be controlled to freely adjust the hydrophilicity of the polymer according to the intended application. That is, the polymer design can be tailored to the required biocompatibility in the application of the polysiloxane.

Also, free from the influence of the phosphorylcholine groups, the polysiloxane can acquire required functions by means of the introduction of hydrophobic groups and such, and then any quantity of phosphorylcholine groups can be added to easily obtain the target functional polymer material.

In the method of the present invention, the compound containing the aldehyde derivative obtained by the oxidative ring-opening reaction of glycerophosphorylcholine is obtained by oxidative ring-opening of the prior art glycerophosphorylcholine group by means of a prior art method, which is a very easy step. This reaction uses periodic acid or periodate to oxidize 1,2-diol to open the bond and obtain two aldehyde derivatives; in this particular method, a phosphorylcholine aldehyde derivative and formaldehyde are produced. The reaction is usually carried out in water or in an organic solvent containing water. The reaction temperature is between 0° C. to room temperature. The aldehyde derivative may go through an equilibrium reaction in water to become a hydrate, but this does not affect the subsequent reaction with the amine.

Selection of the polysiloxane having amino groups is not limited in particular. It suffices if the side chains of the polysiloxane have amino groups with which the aldehyde derivative obtained by the oxidative ring-opening reaction of glycerophosphorylcholine can react. The polysiloxane may have a substituent such as an alkyl group or phenyl group; such a substituent may have an amino group.

The amino group may either be primary or secondary. The amino group can be introduced to the polysiloxane by means of a prior art method or a method that will be developed in the future. Amino-modified polysiloxane, either prior art or developed in the future can be used, too. There is no limitation in terms of the molecular weight of the amino-modified polysiloxane; polysiloxane of any molecular weight can be used.

Examples include an amino-modified polysiloxane represented by the following general formula.

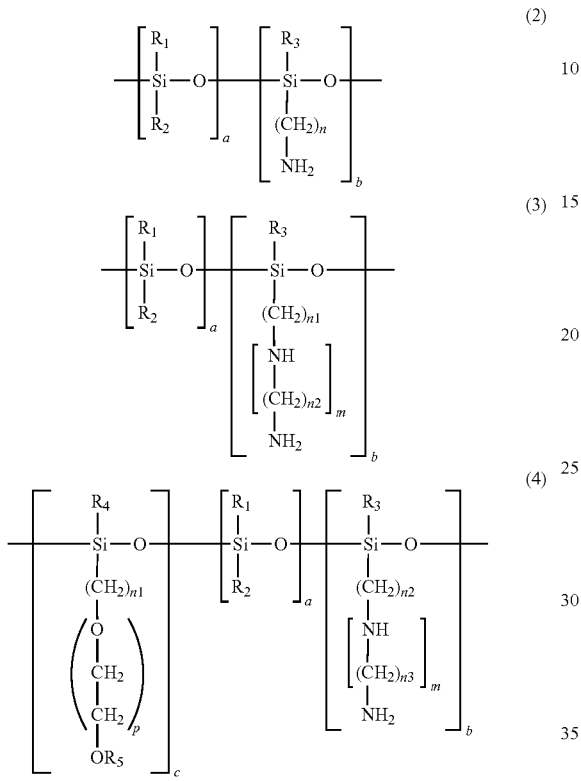

In the formulas above, $R_1$, $R_2$, $R_3$, and $R_4$ independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $R_5$ denotes a hydrogen atom or an alkyl group having 1-22 carbon atoms; n denotes an integer 1-22; $n_1$, $n_2$, and $n_3$, independently of each other, denote an integer 1-22; m denotes an integer 0-10; p denotes an integer 1-30.

Also, a, b, and c denote constituent units of the polysiloxane, that is, the polymer has a units, b units, and c units. Other constituent units may be contained in addition to polymers composed only of a units and b units and polymers composed only of a units, b units, and c units. Also, a units, b units, and c units may either be arranged in a random fashion or in blocks.

When a, b, and c are represented by numbers, they denote molar ratios (polymer composition) of the corresponding constituent units.

The polysiloxane of the present invention is a polysiloxane wherein the phosphorylcholine group represented by formula (1) is added to all or part of amino groups in the aforementioned formula. The ends of the polymer may be anything: for example, a hydroxyl group, alkyl group, hydrogen, and an alkoxy group.

Preferable amino-modified polysiloxanes include a polysiloxane in which $R_1$, $R_2$, and $R_3$ are all methyl groups in formulas (2) and (3) and a polysiloxane in which $R_1$, $R_2$, $R_3$, and $R_4$ are all methyl groups and $R_5$ is hydrogen.

The preparation method of the present invention can use any amino-modified polysiloxane that is suitable for the intended application and allows easy preparation of a polysiloxane that has the phosphorylcholine group represented by the aforementioned formula (1) added to all or part of its amino groups.

Specifically, a polysiloxane composed of constituents a and b represented by the following formulas and a polysiloxane composed of constituents a, b, and c are preferably prepared. These polysiloxanes may contain a constituent b' that does not have a phosphorylcholine group added to its amino groups. That is, they are polysiloxanes comprising an amino-modified polysiloxane that has a phosphorylcholine group added to some of its amino groups. The number of phosphorylcholine groups added to a polysiloxane can be easily adjusted by adjusting the mole number of the aldehyde derivative containing a phosphorylcholine group used for the reaction.

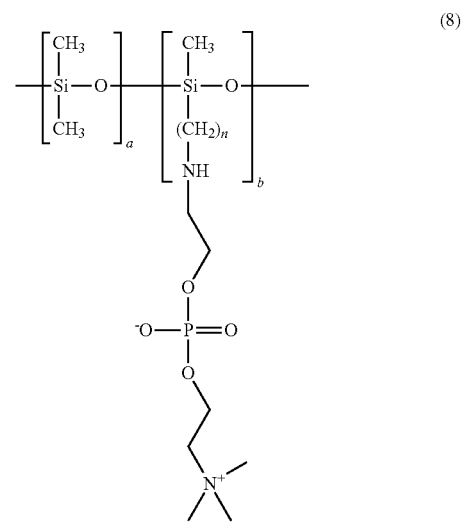

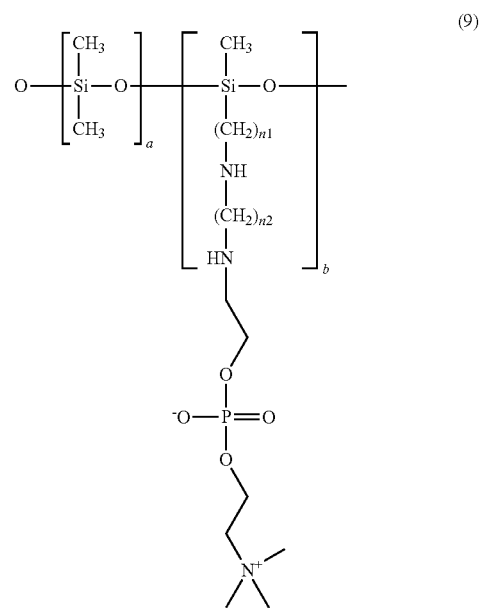

-continued

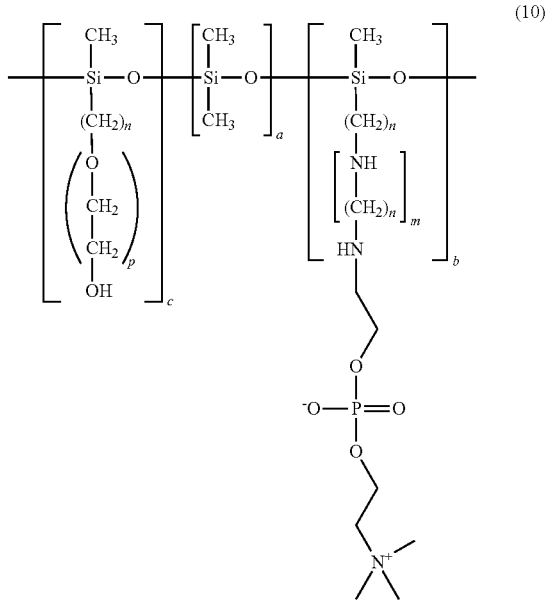

The reductive amination reaction for bonding the aldehyde derivative (or hydrate derivative) obtained by the oxidative ring-opening reaction of glycerophosphorylcholine to the amino groups of a polysiloxane can be carried out easily by stirring both of them in a solvent. This reaction is carried out by dissolving these two in water or alcohol (a third organic solvent ingredient can be mixed in, too) to form an imine and reducing it with a reducing agent to obtain a secondary amine. For the reducing agent, a mild reducing agent such as sodium cyanoboronate is preferable, but other reducing agents can be used as long as the phosphorylcholine is stable. The reaction is usually carried out at 0° C. to room temperature, but heating may be done depending on the situation.

Using the aforementioned preparation method, a polysiloxane containing a desired amount of phosphorylcholine groups in the hydrophilic portion is easily obtained. The molecular weight of the polysiloxane of the present invention can be any value. By using a polysiloxane having an optimum average molecular weight for the application, a polysiloxane containing a phosphorylcholine group having any molecular weight can be prepared. For example, a polysiloxane having a weight average molecular weight of 1,000-500,000 (standard polystyrene equivalent, measured with GPC) can be obtained.

FIG. 1 shows a scheme for preparing a monofunctional aldehyde derivative containing a phosphorylcholine group.

Figure 2:
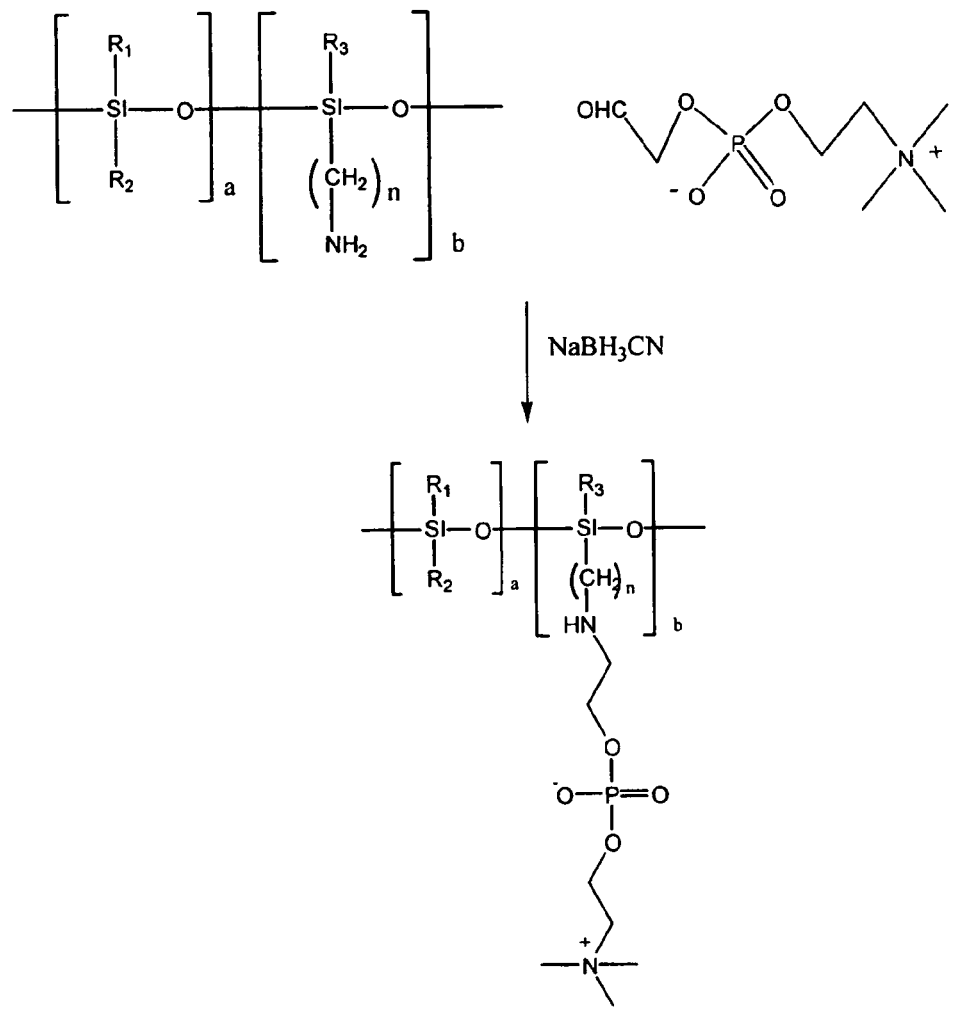
FIG. 2 shows a scheme for preparing a polysiloxane containing a phosphorylcholine group by means of a macromolecular reaction.

FIG. 2 shows a preparation scheme for the polysiloxane of the present invention.

For the hydrophilic portion of the polysiloxane of the present invention other than the polysiloxane group, a prior art method can be used to introduce, for example, a carboxylate group, hydroxyl group, primary-tertiary amine group, sulfonate group, phosphate group, polyoxyethylene group, ammonium group, amide, carboxybetaine, and saccharide.

As for the hydrophobic portion, cyclic alkyls such as cholesterol, alkyl groups containing unsaturated bonds such as oleyl, hydrocarbon type aromatics such as naphthalene rings and pyrene, hetero type aromatics such as pyridine rings, imidazole, thiazole, and indole can be introduced to create a design suitable for the application. The hydrophobic group can bond directly to the main chain with the ester, ether, amide, urethane, or urea bond, or indirectly via a spacer. Examples of the spacer include hydrophilic polyethyleneoxide, hydrophobic polypropyleneoxide, and straight chain alkyls having 2-22 carbon atoms.

The functionality of the polysiloxane can be freely designed by adjusting the type and content of the hydrophilic portion and the hydrophobic portion.

The polysiloxane of the present invention is superior in biocompatibility and moisture retention, and is useful as a polymer material for medical use. Specifically, it is useful in artificial organs, biomembranes, coating agents for medical tools, drug delivery, cosmetic ingredients, etc. It is particularly superior in the skin softening effect, moisture retaining effect, and the transdermal absorption of drugs in an endermic liniment.

EXAMPLES

The present invention is described in detail below by referring to Examples. The present invention is not limited to the following Examples. The composition of each constituent unit of the polysiloxane of the present invention can be determined by NMR. The blend ratios in the endermic liniment recipes for which the effect is verified are in mass percentage units of the total amount.

Synthesis Example 1

An Aldehyde Derivative Containing a Phosphorylcholine Group

L-α-glycerophosphorylcholine (450 mg) is dissolved in 15 ml of distilled water and cooled in an ice water bath. Sodium periodate (750 mg) is added and two hours of stirring is carried out. Next, ethylene glycol (150 mg) is added and overnight stirring is carried out. The reaction solution is vacuum-concentrated and vacuum-dried and the target substance is extracted with methanol.

Figure 3:
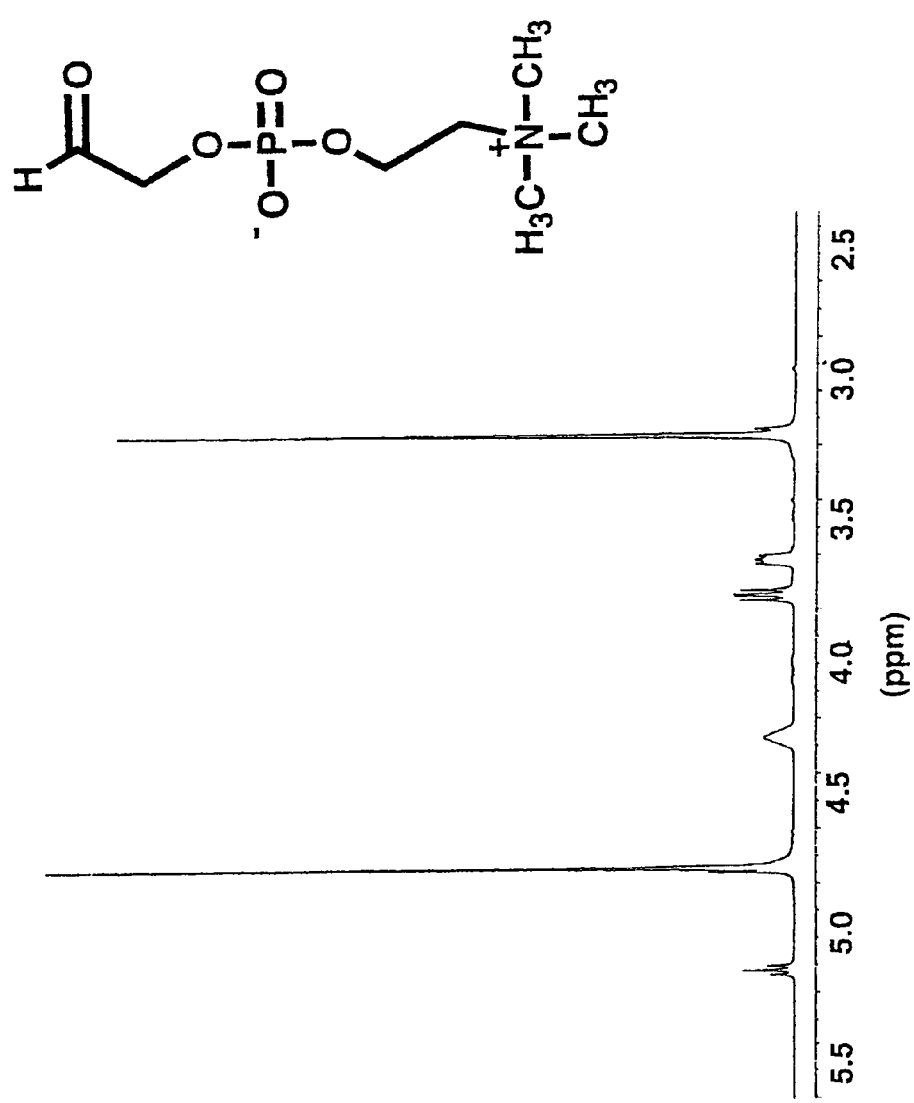
FIG. 3 shows a structural formula and NMR spectrum of Synthesis example 1.

The structural formula and the NMR spectrum are shown in FIG. 3.

Example 1

Figure 4:
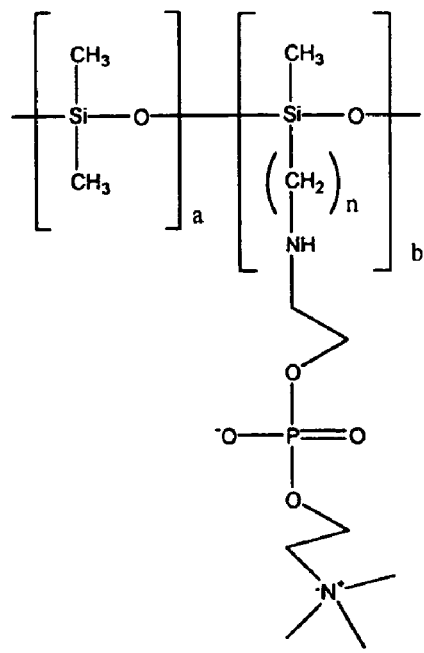
FIG. 4 is the polysiloxane of Example 1.
Figure 7:
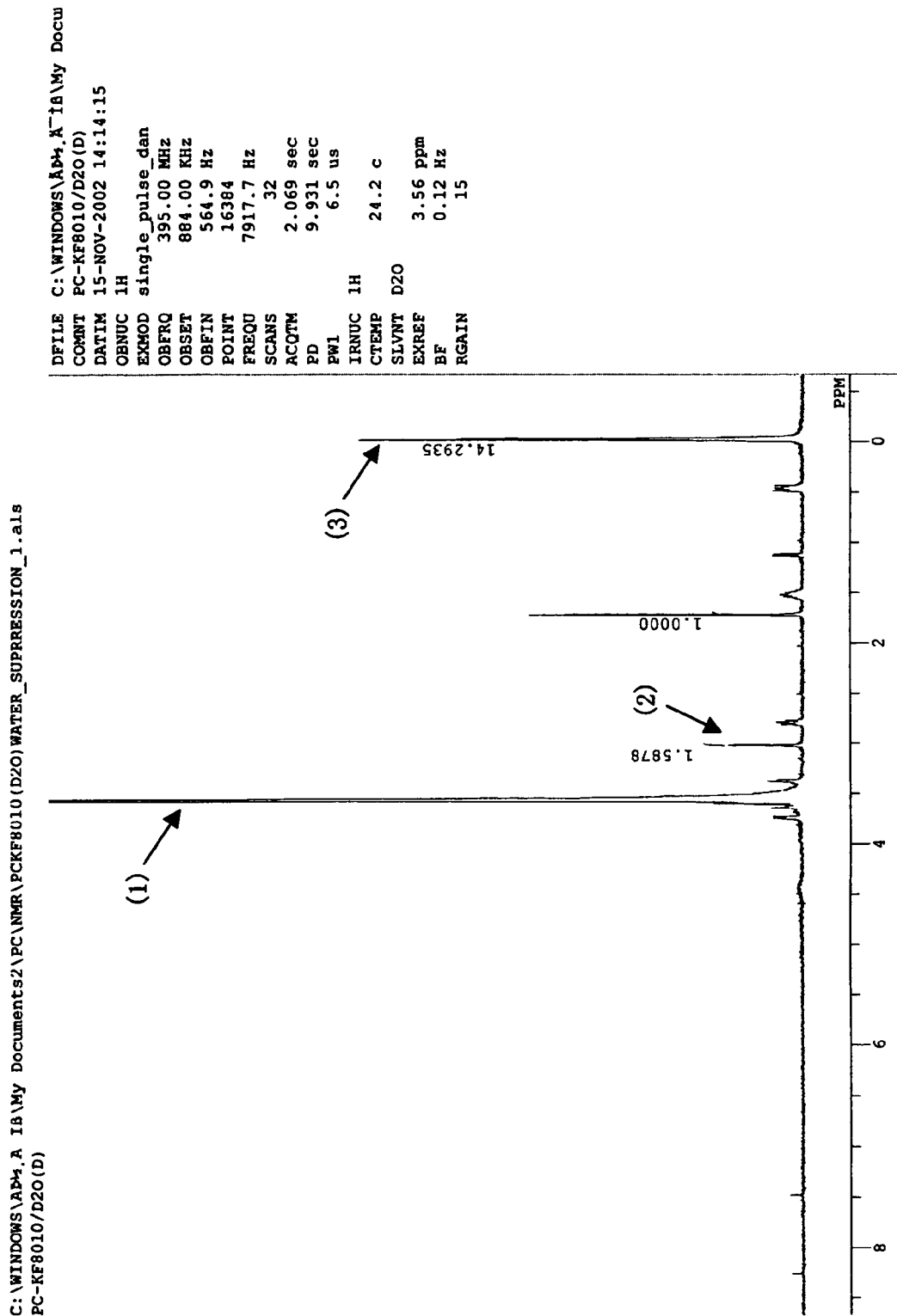
FIG. 7 shows a $^1$H NMR chart of the polysiloxane obtained in Example 1.

Synthesis of Polyalkylsiloxane Containing a Phosphorylcholine Group 1 g of amino-modified polydimethylsiloxane {commercial product KF-86 from Shin-Etsu Chemical Co., Ltd. : $R_1$, $R_2$, $R_3$=$CH_3$, n=2-22 in formula (2), average molecular weight 50,000} is dissolved in methanol (50 ml), to which 0.5 g of the aldehyde derivative in Synthesis example 1 is added, followed by 5 hours of stirring at room temperature. After cooling with ice, sodium cyanoborate hydride (250 mg) is added, followed by overnight stirring. The target substance (0.95 g) is obtained after purification by means of dialyzation and lyophilization. The obtained polysiloxane is shown in FIG. 4. For this, a:b=50:1. A $^1$H NMR chart of the obtained polysiloxane is shown in FIG. 7. Solvent: Heavy water, standard peak: 1,4-dioxane, peak assignment: (1) 1,4-dioaxane, (2)

phosphorylcholine (quaternary ammonium), (3) siloxane (methyl). A peak (2) originated by the phosphorylcholine group appears.

Example 2

Polysiloxane Containing a Phosphorylcholine 1 g of amino-modified polydimethylsiloxane {commercial product X-22-3939A from Shin-Etsu Chemical Co., Ltd. : $R_1$, $R_2$, $R_3$, $R_4$=$CH_3$, $R_5$ is hydrogen, $n_1$, $n_2$, $n_3$=2-22 in formula (4), average molecular weight 50,000} is dissolved in methanol (50 ml), to which 0.5 g of the aldehyde derivative in Synthesis example 1 is added, followed by 5 hours of stirring at room temperature. After cooling with ice, sodium cyanoborate hydride (250 mg) is added, followed by overnight stirring. The target substance (0.9 g) is obtained after purification by means of dialyzation and lyophilization.

Figure 5:
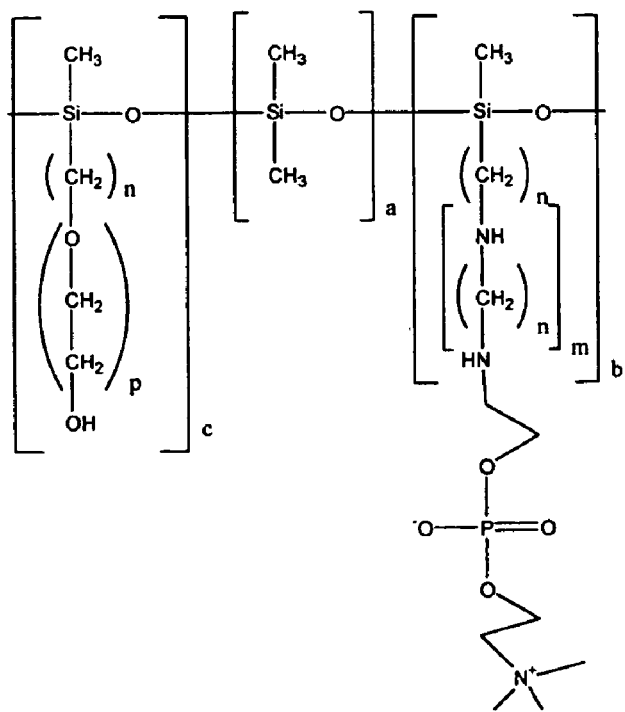
FIG. 5 is the polysiloxane of Example 2.

The obtained polysiloxane is shown in FIG. 5. For this, a:b:c is unknown.

Example 3

Polysiloxane Containing a Phosphorylcholine 1 g of amino-modified polydimethylsiloxane {commercial product KF-393 from Shin-Etsu Chemical Co., Ltd. : $R_1$, $R_2$, $R_3$=$CH_3$, $n_1$, $n_2$=2-22 in formula (2), average molecular weight 3000} is dissolved in methanol (50 ml), to which 0.5 g of the aldehyde derivative in Synthesis example 1 is added, followed by 5 hours of stirring at room temperature. After cooling with ice, sodium cyanoborate hydride (250 mg) is added, followed by overnight stirring. The target substance (0.95 g) is obtained after purification by means of dialyzation and lyophilization.

Figure 6:
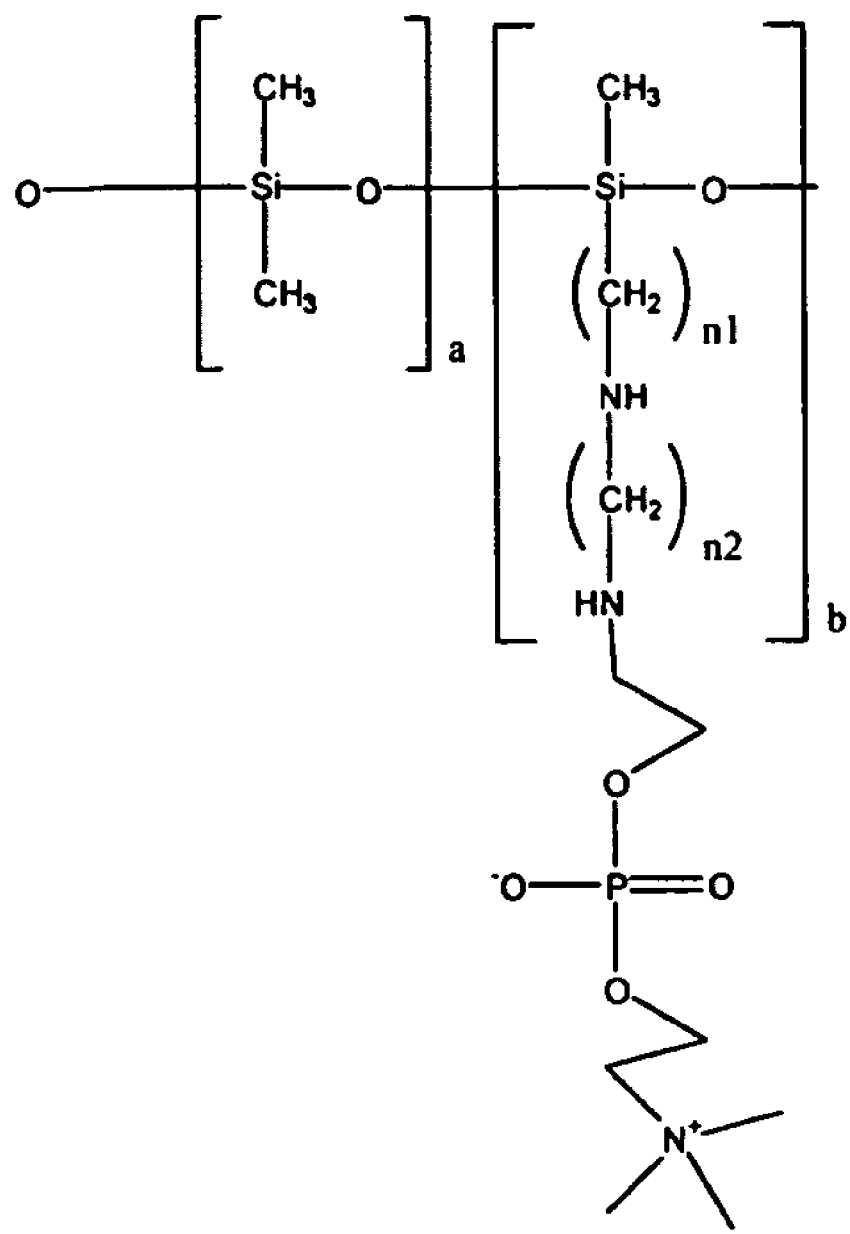
FIG. 6 is the polysiloxane of Example 3.
Figure 8:
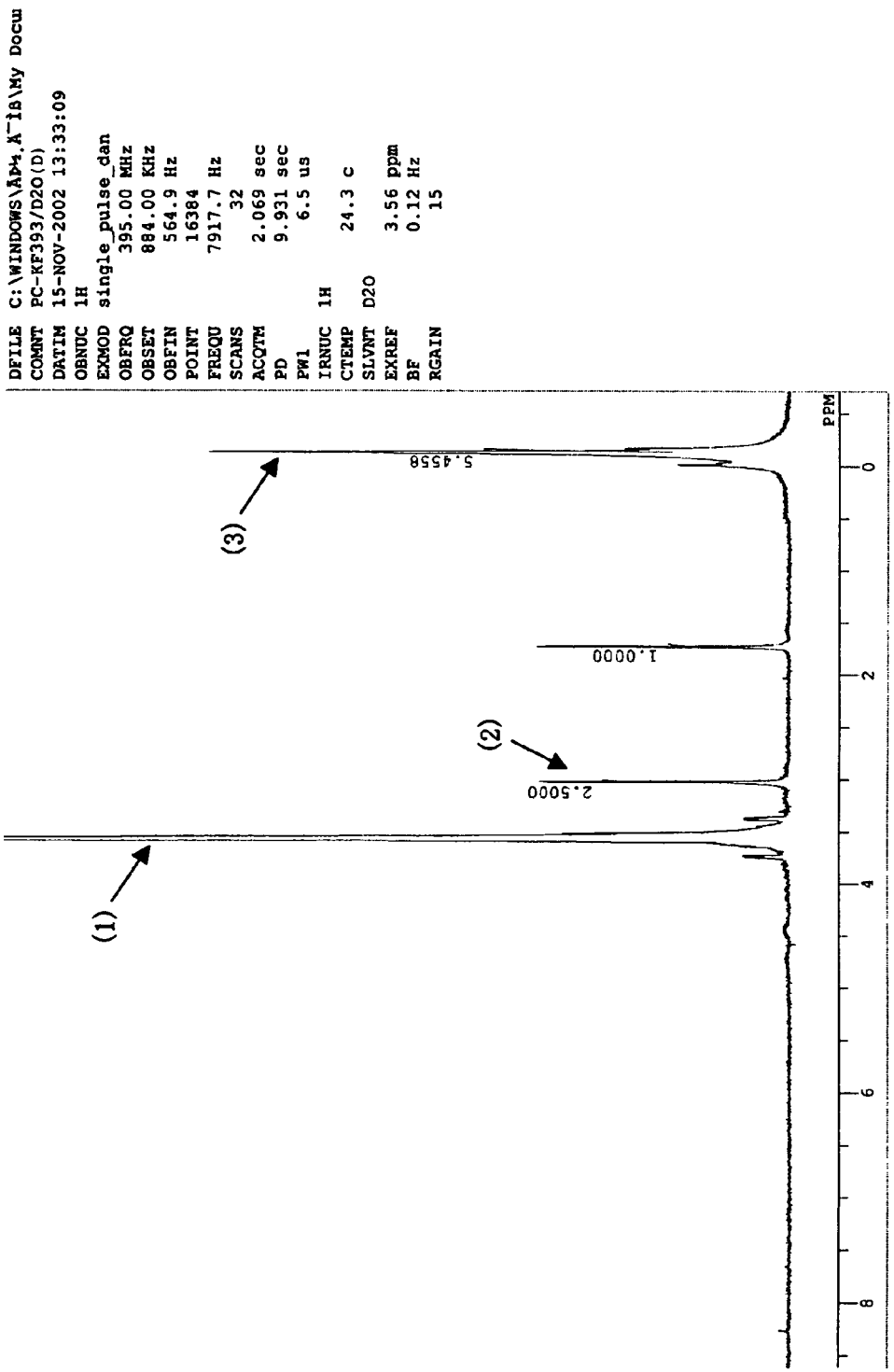
FIG. 8 shows a $^1$H NMR chart of the polysiloxane obtained in Example 3.

The obtained polysiloxane is shown in FIG. 6. For this, a:b=5:1. A $^1$H NMR chart of the obtained polysiloxane is shown in FIG. 8. Solvent: Heavy water, standard peak: 1,4-dioxane, peak assignment: (1) 1,4-diaoxane, (2) phosphorylcholine (quaternary ammonium), (3) siloxane (methyl). A peak (2) originated by the phosphorylcholine group appears.

(1) The Moisture Retaining Effect and the Skin Softening Effect

Moisture retaining essences containing the polymer of the aforementioned Examples are prepared and comparison is made in terms of the moisture retention duration and the skin softening effect. The recipes and results are shown in Table 1.

The evaluation is based on average scores of sensory evaluation by 20 specialists using the following criteria.

<Moisture Retention Effect>
3 points: The moisture retention effect lasts 10 hours or more after the application.
2 points: The moisture retention effect lasts 4 hours or more and less than 10 hours after the application.
1 point: The moisture retention effect lasts 1 hour or more and less than 4 hours after the application.
0 point: The moisture retention effect lasts less than 1 hour.

<Skin Softening Effect>
3 points: The skin becomes very softer after 1 week of use.
2 points: The skin becomes somewhat softer after 1 week of use.
1 point: The skin condition does not change after 1 week of use.
0 point: The skin becomes harder after 1 week of use.

<Evaluation>

TABLE 1

|  | Comparative example 1 | Comparative example 2 | Comparative example 3 | Example 1 | Example 2 |
|---|---|---|---|---|---|
| Sorbitol | 8 | 8 | 8 | 8 | 8 |
| 1,3-butylene glycol | 5 | 5 | 5 | 5 | 5 |
| Ethanol | 7 | 7 | 7 | 7 | 7 |
| POE oleyl alcohol ether | 1 | 1 | 1 | 1 | 1 |
| Olive oil | 0.2 | 0.2 | 0.2 | 0.2 | 0.2 |
| Purified water | 78.8 | 78.7 | 78.7 | 78.7 | 78.7 |
| Skin softening ingredient | None | Elastin 0.1 | Sodium hyaluronate 0.1 | Example 1 0.1 | Example 2 0.1 |
| Skin softening effect | Δ | ○ | ○ | ◎ | ◎ |
| Moisture retention effect | X | Δ | ○ | ◎ | ◎ |

◎: The average score is 2.5-3 points.
○: The average score is 2 points or more and less than 2.5 points.
Δ: The average score is 1 point or more and less than 2 points.
X: The average score is less than 1 point.

The results shown in Table 1 above indicate that the polysiloxane of the present invention has a superior moisture retention effect and skin softening effect and functions as an ingredient for cosmetics.

(2) The Transdermal Absorption Accelerating Effect

The transdermal absorption accelerating effect for drugs in an endermic liniment is tested with the following method disclosed in Japanese Patent Laid-Open 2002-71682.

The test is carried out in the in vitro fashion. The skin of a miniature pig is used as the skin model.

Arbutin is used for the drug. A simple aqueous solution of arbutin (Comparative example 4) and a solution that is this solution with the polysiloxane of Example 1 or Example 2 added to it are applied to the skin of a miniature pig, followed by a 6 hour incubation at 37° C.; the epidermis is subjected to solvent extraction and the drug contained in a unit weight is quantified by means of HPLC to obtain the transdermal absorption for comparison.

The results are shown in Table 2.

The transdermal drug absorption ratio in Table 2 stands for (Arbutin absorption in Example recipe/Arbutin absorption in Comparative example 4 recipe).

These results indicate that the solutions containing Example 1 and Example 2 have accelerated transdermal absorption of arbutin and therefore the polysiloxane of the present invention has a superior transdermal absorption accelerating effect for drugs in an endermic liniment.

TABLE 2

|  | Comparative example 4 | Example 1 | Example 2 |
|---|---|---|---|
| Example 1 |  | 0.5 |  |
| Example 2 |  |  | 0.5 |
| Arbutin | 6 | 6 | 6 |
| Physiological saline | 94 | 93.5 | 93.5 |
| Transdermal drug absorption ratio (Absorption in Example recipe/Absorption in Comparative example 4 recipe) | 1 | 1.6 | 1.75 |

INDUSTRIAL APPLICABILITY

The phosphorylcholine group-containing polysiloxane of the present invention has high biocompatibility and moisture retention and is a useful polymer material; it has a variety of applications such as artificial organs, biomembranes, coating agents for medical tools, drug delivery, and as cosmetic ingredients.

The manufacturing method of the present invention using a macromolecular reaction has a great advantage in that it allows flexible designing of a polysiloxane ideal for biocompatible polymer materials for specific applications.

Free from the influence of a phosphorylcholine group, the structure of the main chain polysiloxane can be freely designed to obtain a material best suitable for the application, and then any quantity of phosphorylcholine groups can be added to easily obtain the target functional polysiloxane material.

A polysiloxane containing a phosphorylcholine group is superior in the moisture retention, skin softening effect, and transdermal absorption of drugs and therefore it can be blended into an endermic liniment such as cosmetics to provide a superior endermic liniment.

The invention claimed is:

1. A polysiloxane having repeating units a and b represented by the following formula (5):

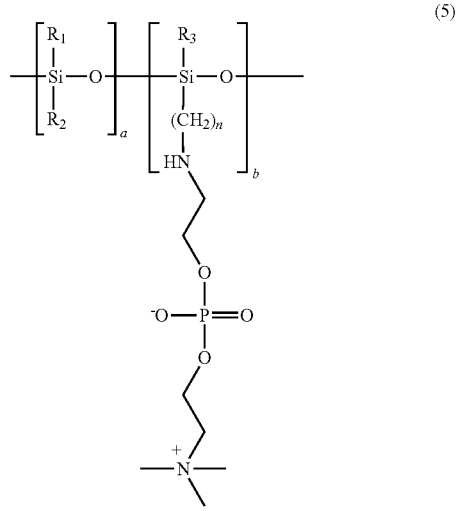

(5)

wherein $R_1$, $R_2$, and $R_3$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group, n denotes an integer 1-22; and a and b denote constituent units of the polysiloxane, wherein said polysiloxane is obtained by introducing a phosphorylcholine group represented by the following formula (1):

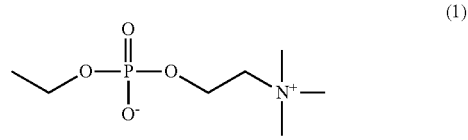

(1)

to some or all of the amino groups of the amino-modified polysiloxane having repeating units a and b represented by the following formula (2):

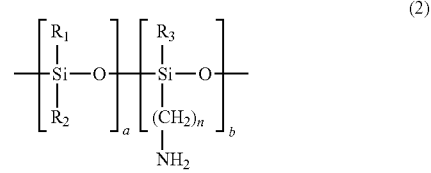

(2)

wherein $R_1$, $R_2$, and $R_3$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group, n denotes an integer 1-22, and a and b denote constituent units of the polysiloxane.

2. A polysiloxane having repeating units a and b represented by the following formula (6):

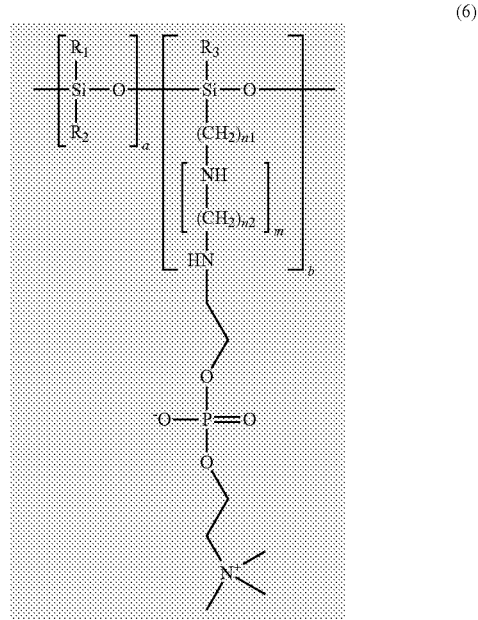

(6)

wherein $R_1$, $R_2$ and $R_3$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $n_1$ and $n_2$, independently of each other, denote an integer 1-22; m denotes an integer 0-10; and a and b denote constituent units of the polysiloxane, and wherein said polysiloxane is obtained by introducing the phosphorylcholine group represented by the following formula (1):

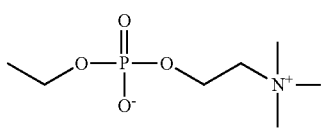 (1)

to some or all of the amino groups of the amino-modified polysiloxane having repeating units a and b represented by the following formula 3:

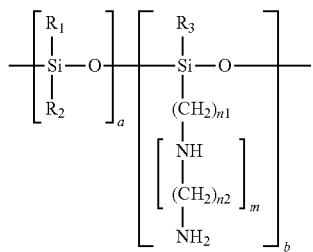 (3)

wherein $R_1$, $R_2$, and $R_3$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $n_1$ and $n_2$, independently to each other, denote an integer 1-22, m denotes an integer 0-10; and a and b denote constituent units of the polysiloxane.

3. A polysiloxane having repeating units a, b and c represented by the following formula (7):

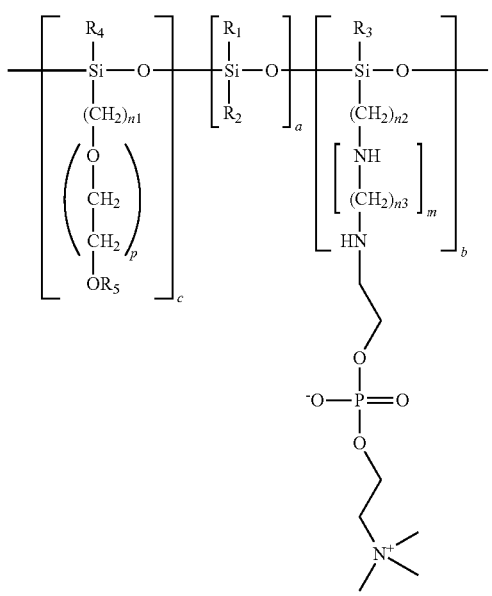 (7)

wherein $R_1$, $R_2$, $R_3$, and $R_4$ independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $R_5$ denotes a hydrogen atom or an alkyl group having 1-22 carbon atoms; n denotes an integer 1-22; $n_1$, $n_2$, and $n_3$, independently of each other, denote an integer 1-22; m denotes an integer 0-10; p denotes an integer 1-30; and a, b and c denote constituent units of the polysiloxane, and wherein said polysiloxane is obtained by introducing the phosphorylcholine group represented by the following formula (1):

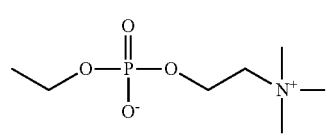 (1)

to some or all of the amino groups of the amino-modified polysiloxane having repeating units a and b represented by the following formula 4:

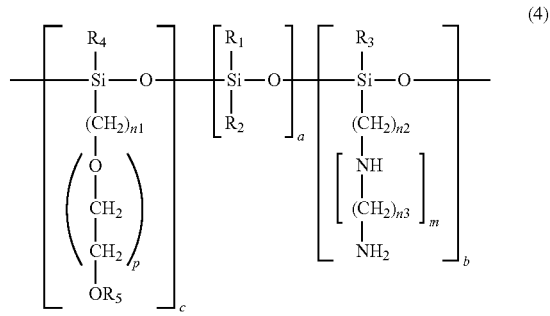 (4)

wherein $R_1$, $R_2$, $R_3$ and $R_4$, independently of each other, denote an alkyl group or perfluoroalkyl group having 1-22 carbon atoms, an alkoxysilyl group having 1-6 carbon atoms via an alkylene group having 1-6 carbon atoms, a phenyl group, or hydroxyl group; $n_1$, $n_2$, and $n_3$, independently to each other, denote an integer 1-22; m denotes an integer 0-10, p denotes an integer 1-30, and a, b, and c denote constituent units of the polysiloxane.

* * * * *